United States Patent [19]

Harautuneian

[11] 3,989,571
[45] Nov. 2, 1976

[54] METHOD OF MAKING A SMOOTH TIPPED ENDOTRACHEAL TUBE

[75] Inventor: Andrew Harautuneian, Westlake Village, Calif.

[73] Assignee: American Hospital Supply Corporation, Evanston, Ill.

[22] Filed: Nov. 18, 1974

[21] Appl. No.: 524,707

Related U.S. Application Data

[62] Division of Ser. No. 353,244, April 23, 1973, Pat. No. 3,862,635.

[52] U.S. Cl. .......................... 156/250; 128/349 B; 128/351; 156/258; 156/294
[51] Int. Cl.² .................. A61M 25/00; B29C 17/10; B32B 31/04; B32B 31/18
[58] Field of Search ........... 156/251, 267, 293, 294, 156/250, 258; 128/349 B, 349 R, 350 R, 350 V, 351

[56] References Cited
UNITED STATES PATENTS

| 3,292,627 | 12/1966 | Harauteneian | 128/349 B |
| 3,384,089 | 5/1968 | Shriner | 128/350 V |
| 3,460,541 | 8/1969 | Doherty | 128/351 |
| 3,625,793 | 12/1971 | Sheridan et al. | 156/294 |
| 3,734,100 | 5/1973 | Walker et al. | 128/349 B |

Primary Examiner—Caleb Weston
Attorney, Agent, or Firm—Larry N. Barger; Robert T. Merrick

[57] ABSTRACT

An endotracheal tube including a preformed inflatable plastisol balloon telescopically fitted over and secured to a forward end portion of a dual-lumen tube. The inflatable balloon is formed with an elongated forward collar which is fitted onto the dual-lumen tube. The tube and collar are simultaneously severed along a biased cut to provide an open front end of the endotracheal tube. The forward collar and dual-lumen tube are then fused into a generally homogeneous mass to provide a smooth exterior sliding surface at the forward end portion of the endotracheal tube.

10 Claims, 5 Drawing Figures

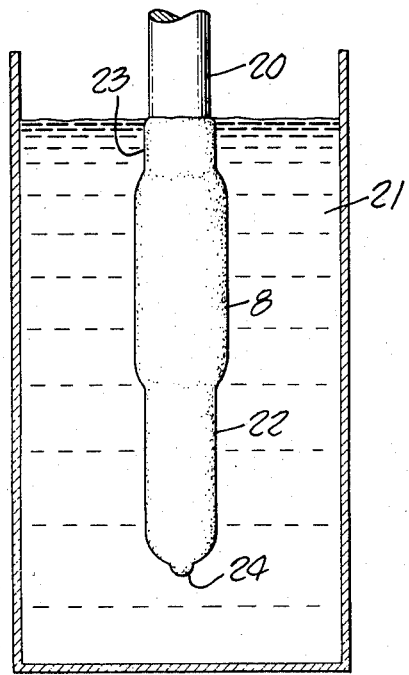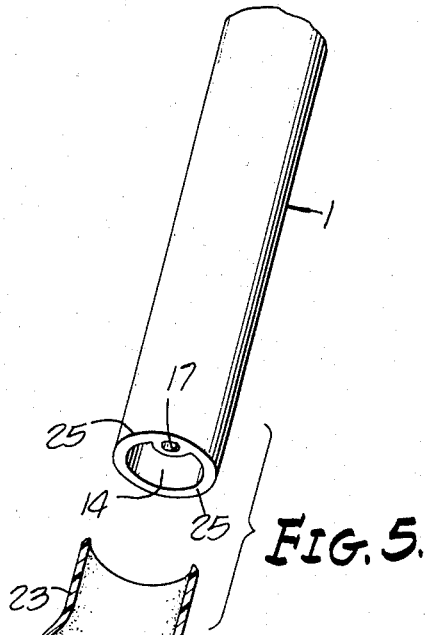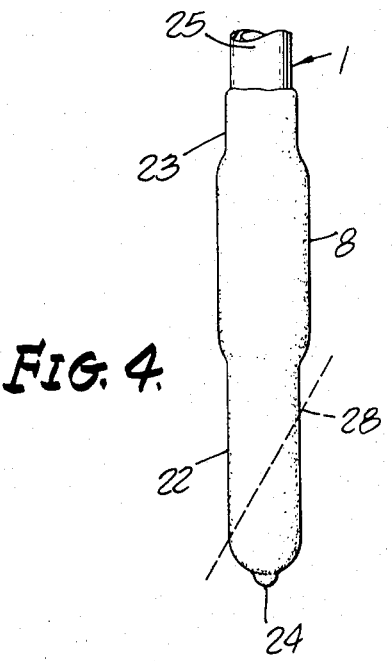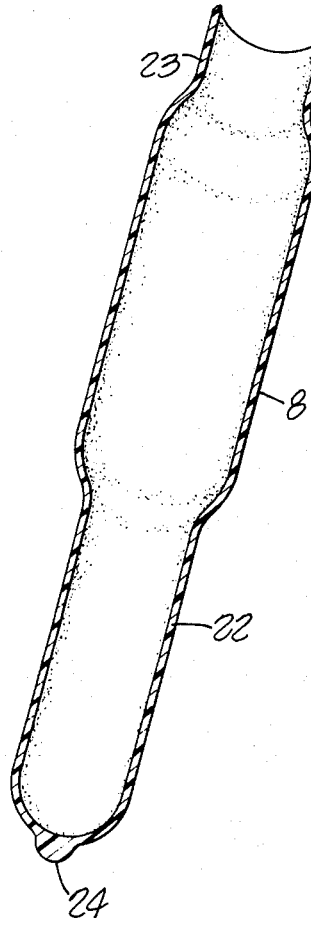

METHOD OF MAKING A SMOOTH TIPPED ENDOTRACHEAL TUBE

This is a division of application Ser. No. 353,244; filed Apr. 23, 1973 now U.S. Pat. No. 3,862,635.

BACKGROUND

When a patient is anesthetized with inhalable gaseous anesthesia various devices are used to direct the anesthesia into the patient's lungs. One type device involves a mask that fits over the patient's nose and mouth and connects with an anesthesia machine. Another device includes a nasal cannula where the anesthesia is directed through the nasal passage and into the patient's lungs. Still another, and becoming more widely used, is an endotracheal tube.

An endotracheal tube is essentially a large-diameter tube inserted in through the patient's mouth and fed down through the trachea to where it terminates right above the bronchial branch connected to the lungs. This endotracheal tube is then connected to an anesthesia machine. Many physicians believe that the endotracheal tube method provides a more accurate control of administering the anesthesia to the patient.

When anesthesia is fed through the endotracheal tube in the patient's trachea a structure is required to seal the outer surface of the endotracheal tube with the trachea. This is to keep anesthesia gases from escaping back between the endotracheal tube and the trachea. A common structure for sealing the endotracheal tube to the trachea is an inflatable balloon. This is sometimes called the "cuff" or tracheal balloon of an endotracheal tube. Because the endotracheal tube and balloon are in a tender area of the patient's trachea it is desires that the tube and balloon be made of a nonirritating material. Previous rubber cuffs and tubes had the disadvantage of containing accelerators and vulcanizing agents, which could irritate the trachea.

Preferred endotracheal tubes are made of a thermoplastic or plastisol material that do not require vulcanizing agents and cause less irritation to the patient.

In the past these endotracheal tubes have been made by preforming a plastisol cuff or balloon and then securing this balloon to a flexible tube. One of the major problems in securing the balloon to the tube involved the joint between the balloon and the tube. Because the endotracheal tube must slide down past the vocal cords it is important to make the forward end of the endotracheal tube as smooth as possible. One of the main problems with previous endotracheal tubes was the annular ridge formed at the forward juncture of the inflatable sleeve and the dual-lumen tube. It is to this tube and inflatable balloon joint that this invention relates.

SUMMARY OF THE INVENTION

This invention overcomes the problems of joining a plastisol preformed inflatable balloon to a dual-lumen thermoplastic insertion tube to create a smooth sliding external surface. The inflatable plastisol sleeve or balloon of this invention is formed with an enlarged inflatable center portion and an elongated forward collar portion. Rearwardly of the large center portion there is also a rear collar portion. The dual-lumen tube is inserted in through the rear collar, the enlarged center portion and into the elongated forward collar portion. Next, the forward collar and dual-lumen tube are simultaneously cut along a diagonal bias plane surface to develop an open forward end of the endotracheal tube. Finally, the forward end of the endotracheal tube with the coterminous forward collar of the balloon and dual-lumen tube are heat fused in an induction heating die. The endotracheal tube is then removed from the heating die to provide a generally homogeneous rounded forward end portion of the endotracheal tube. There is no visible joint or ridge between the forward collar and the insertion tube, but only a smooth sliding surface.

THE DRAWINGS

FIG. 3 is a front elevational view showing a step in forming the plastisol inflatable sleeve with its elongated forward collar;

FIG. 4 is a side elevational view of the combined inflation sleeve and thermoplastic insertion sleeve showing how they are simultaneously severed at the elongated front collar portion; and FIG. 5 is an enlarged section view of the preformed inflation sleeve and the dual-lumen theremoplastic tube immediately before they are assembled.

DETAILED DESCRIPTION

Figure 1:
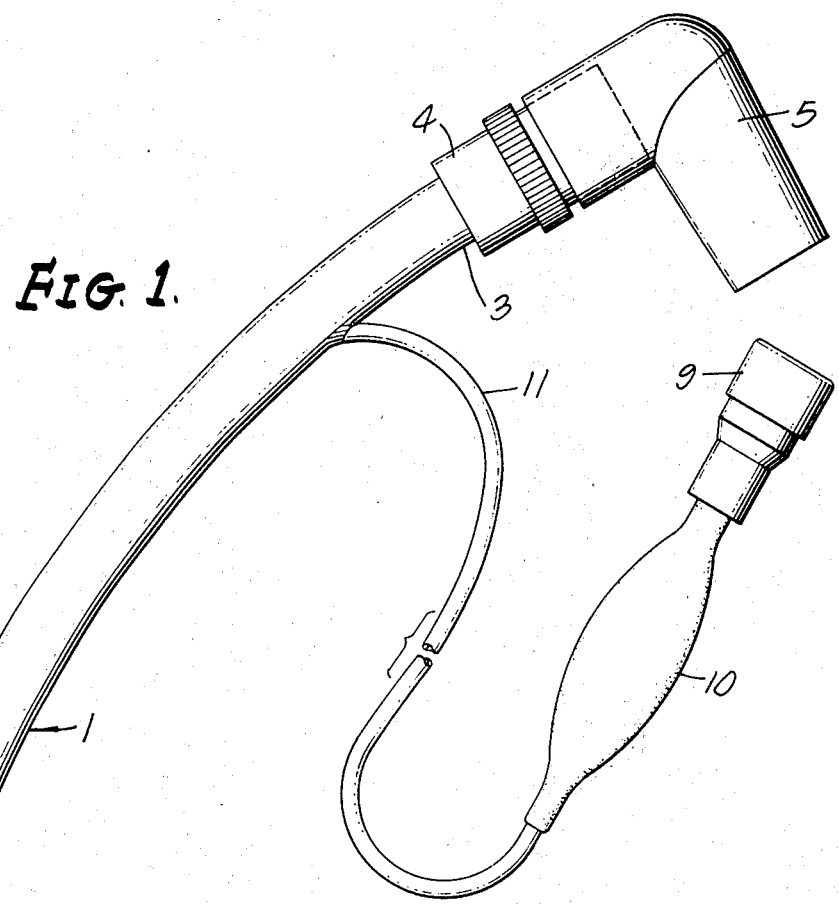
FIG. 1 is a side elevational view of the endotracheal tube showing it complete and ready for attachment to an anesthesia machine.

Referring to these above-mentioned drawings, the completed endotracheal tube shown in FIG. 1 includes a dual-lumen thermoplastic insertion tube 1 that extends between a forward tip portion 2 and a rearward end 3. At rear end 3 is attached an adapter 4 which connects with an elbow element 5. This elbow 5 is adapted to connect directly to an anesthesia machine (not shown) that feeds anesthesia gas into the endotracheal tube at a precisely controlled rate and concentration.

Adjacent a forward end of the dual-lumen tube is an inflatable tracheal balloon 6. This balloon extends from a forward tip 2 of the endotracheal tube, where it is integrally fused with the dual-lumen insertion tube, to a rear end 7 of the tracheal balloon. The tracheal balloon has a preformed enlarged central portion 8 that is spaced from the dual-lumen tube 1 in its normal uninflated condition. To further inflate the enlarged central portion 8, air or liquid is injected through a valve member 9, a pilot balloon 10, and through a side arm 11 that connects to an inflation lumen. This inflation lumen communicates with an interior of the enlarged central portion 8 of the inflation sleeve. Thus, as air or liquid is forced in through the check valve 9 the center portion 8 of the tracheal balloon is inflated. The pilot balloon 10 likewise swells and gives a visual indication that the enlarged central portion 8 is inflated. Pilot balloon 10 is outside the patient and readily visible at all times while inflated central portion 8 is in the patient's trachea and not readily visible.

Figure 2:
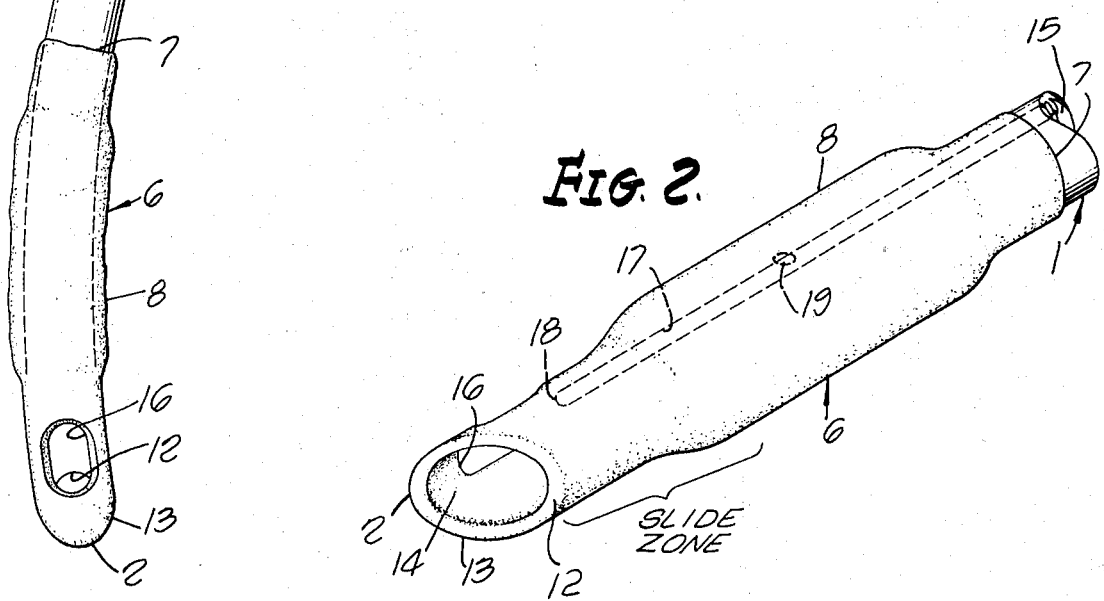
FIG. 2 is an enlarged perspective view of the inflatable sleeve portion of the endotracheal tube.

In the perspective view of FIG. 2 the enlarged inflatable tracheal balloon is shown in more detail. The endotracheal tube terminates in the forward tip portion 2 that extends rearwardly to a heel portion 12 of the endotracheal tube. This tip 2 and heel portion 12 lie along a bias plane surface at an annular lip 13 that surrounds an open forwardly facing end port 14. End port 14 communicates with a main lumen 15 that extends longitudinally through the dual-lumen tube 1. Anesthesia gas entering through elbow connector 5 from an anesthesia machine passes through main lumen 15 and exists through forward port 14. If the physician desires to suction the trachea and bronchial area of the patient, he can readily insert a suction catheter or the like through the main lumen 15 and cause it to protrude through forward port 14.

When the endotracheal tube is inserted into the trachea, the forward end portion includes open port 14 that can direct the anesthesia gas. There is also a side port 16 immediately forward of the enlarged central inflatable section of the sleeve. Port 16 provides a safety port for anesthesia gases to exit should forward port 14 become clogged with mucous, etc. Also it is believed that ports 14 and 16 in FIG. 2 each help direct the anesthesia gases to the individual lungs.

In FIG. 2 there is also shown in dotted line the inflation lumen 17 the communicates with the side branch tube 11. It is noted that this inflation lumen 17 is closed off at a forward end portion 18. Also this inflation lumen 17 includes a port 19 that connects the lumen 17 with an interior portion of the inflatable enlarged central portion of the tracheal balloon. Therefore, the enlarged inflatable center section can be inflated or deflated by means of a hypodermic syringe connected to check valve 9.

A very important feature of this invention is best illustrated in FIG. 2, and includes the smoothly contoured external slide zone extending from the forward angularly biased annular lip 13 to the enlarge inflatable central portion of the tracheal balloon. This smooth slide zone includes no abrupt interruption across the forward collar portion of the tracheal balloon.

The tracheal balloon and how it is formed is very critical to this invention. As shown in FIG. 3 the inflatable tracheal balloon is made by dipping a mandrel with an enlarged body segment conforming to the desired internal contour of the inflatable enlarged central portion of the balloon. This mandrel 20 is dipped into a plastisol bath 21. The plastisol begins to build up on the mandrel 20 until the desired thickness of the balloon is obtained.

Next, the mandrel is removed from the polyvinyl chloride plastisol 21. The formed inflatable plastisol sleeve is then cured. Then, the inflatable sleeve is stripped from the mandrel and the preformed balloon has an internal and external configuration shown generally in the enlarged cross-sectional view in FIG. 5. Here is shown the enlarged central portion 8 connected to an elongated forward collar 22 and a rearwardly extending collar 23. The elongated collar 22 is closed at its forward end and includes a small drip portion 24 formed when removing the mandrel from the plastisol dip bath.

The dual-lumen thermoplastic tube is made from an extruded polyvinyl chloride thermoplastic and a forward section is shown in FIG. 5. Here the tube 1 includes an annular wall that defines a main lumen 14; located within wall 25 is a much smaller inflation lumen 17.

Having formed the inflatable plastisol tracheal balloon and the dual-lumen extruded thermoplastic tube, the two units are telescopically fitted together by inserting the dual-lumen tube 1 in through the rear collar 23, enlarged inflatable section 8 and into forward collar 22. Preferably the collars 23 and 22 have an internal diameter slightly smaller than the external diameter of the dual-lumen tube 1. This is so the tracheal balloon will tightly grip the dual-lumen tube. If desired the collars 22 and 23 can be expanded over a tubular mandrel while inserting tube 1 or they can be wetted with a solvent or lubricant.

When the dual-lumen tube 1 and inflatable sleeve 6 are assembled they appear as in FIG. 4. The next step in the production of the novel endotracheal tube is to sever one or both the forward collar 22 and the tube 1 along a biased plane indicated at 28 in FIG. 4. Preferably both are severed simultaneously. Plane 28 forms an angle in the range of 30° to 60° relative to the longitudinal axis of the dual-lumen tube. This leaves both the forward collar 22 and dual-lumen tube 1 with coterminous biasly cut forward end surfaces.

At this time the two collars 22 and 23 can be permanently bonded with air tight joints to the dual-lumen tube 1 by heat fusion such as by induction heating or bonded by solvent adhesive. Preferably the rear end portion of rear collar 23 is rounded and smoothly contoured to the tube at this time. Also side port 16 can now be punched out of the wall of the insertion tube and the overlying tracheal balloon's forward collar.

To form the smooth slide zone shown in FIG. 2 the combined tube 1 and inflatable sleeve section 6 are inserted into a heating mold. This fuses the forward tip into a thermoplastic mass which also fuses shut the forward end 18 of the inflation lumen. When the endotracheal tube is fused, the forward collar 22 becomes integral and generally homogeneous with the dual-lumen tube 1. This creates a smooth rounded forward lip 13 and prevents delamination of the forward collar 22 and the wall 25 of the dual-lumen tube. It forms an externally smooth slide zone as shown in FIG. 2. There is no interruption at a forward end of the collar where it joins to the dual-lumen tube. Thus the endotracheal tube can smoothly slide past a patient's vocal cords with reduced chance of injuring the vocal cords.

In the foregoing specification a specific embodiment has been used to describe the invention. However it is understood by those skilled in the art that certain modifications can be made to this embodiment without departing from the spirit and scope of the invention.

I claim:

1. A method of making a smooth tipped medical tube comprising the steps of: forming a dual-lumen tube; separately forming an inflatable balloon with a permanently enlarged center portion, a forward collar section, and a rearward collar section; inserting the dual-lumen tube into a rear collar section, through the enlarged inflatable section and into the forward collar of the balloon; severing a forward portion of either one or both of the dual-lumen tube and the forward collar so the forward collar and dual-lumen tube are coterminous at a forward end of the medical tube; and forming the forward end portion of the dual-lumen tube and overlying front collar into a smooth, rounded lip with no visible ridge or joint surrounding an open forward end of the medical tube.

2. A method of making an endotracheal tube comprising the steps of: forming an insertion tube with an outer wall, a main lumen, an inflation lumen, and an opening through the outer wall into the inflation lumen; separately forming an inflatable thermoplastic tracheal balloon; telescopically fitting said tracheal balloon over said insertion tube to cover said opening in the tube's wall; securing end portions of the inflatable balloon to the wall of the dual-lumen tube to form two spaced-apart annular airtight joints between the balloon and insertion tube; severing portions of both the tracheal balloon and the dual-lumen tube to form a front end portion of the endotracheal tube that is coterminous with the balloon's front end; and forming the front end surfaces of the severed tracheal balloon and endotracheal tube into a smooth, rounded bonded surface with no visible ridge or joint for easy insertion into a patient.

3. The method as set forth in claim 2 wherein the tracheal balloon and the dual-lumen tube are fused together and the forward lip surface is post formed by heat into a smooth rounded generally homogeneous thermoplastic tip for a smooth sliding insertion into a patient.

4. The method of claim 2, wherein portions of the tracheal balloon and dual-lumen tube are severed simultaneously.

5. The method as set forth in claim 2 wherein the forward end of the endotracheal tube and tracheal balloon is severed at a bias to a longitudinal axis of the insertion tube.

6. The method as set forth in claim 5 wherein the endotracheal tube and tracheal balloon are severed at an angle between 30° and 60° relative to its longitudinal axis.

7. A method for forming a medical tube with attached balloon comprising the steps of:
forming a tube with a longitudinal axis;
separately forming a balloon with a pair of tubular collars at opposite longitudinal ends of the balloon;
inserting said tube into the balloon until both collars are fitted around the tube;
adjusting the longitudinal relationship of the tube and balloon so that one collar of the balloon and the tube have forward ends which are coterminous; and
forming the forward end portions of said one collar, and the tube into a smooth, rounded bonded surface with no visible ridge or joint for easy insertion into a patient.

8. The method of claim 7, wherein the forward ends of said one collar and tube are heat fused into a smooth rounded bonded surface.

9. The method of claim 7, wherein the adjusting step includes simulatenously severing said one collar and the tube.

10. The method of claim 9, wherein the forward end of said one collar has a closed end portion that is severed from a remaining portion of said one collar.

* * * * *